(12) United States Patent
Schneider et al.

(10) Patent No.: US 8,795,148 B2
(45) Date of Patent: *Aug. 5, 2014

(54) SUB-MOTOR-THRESHOLD STIMULATION OF DEEP BRAIN TARGETS USING TRANSCRANIAL MAGNETIC STIMULATION

(75) Inventors: M. Bret Schneider, Portola Valley, CA (US); David J. Mishelevich, Playa del Rey, CA (US)

(73) Assignee: Cervel Neurotech, Inc., Redwood City, CA (US)

( * ) Notice: Subject to any disclaimer, the term of this patent is extended or adjusted under 35 U.S.C. 154(b) by 735 days.

This patent is subject to a terminal disclaimer.

(21) Appl. No.: 12/912,650

(22) Filed: Oct. 26, 2010

(65) Prior Publication Data

US 2011/0098779 A1    Apr. 28, 2011

Related U.S. Application Data

(60) Provisional application No. 61/254,964, filed on Oct. 26, 2009.

(51) Int. Cl.
*A61N 2/02* (2006.01)

(52) U.S. Cl.
USPC .......................................................... 600/14

(58) Field of Classification Search
USPC ........................................ 600/9–15; 607/2–3
See application file for complete search history.

(56) References Cited

U.S. PATENT DOCUMENTS

| | | |
|---|---|---|
| 3,799,164 A | 3/1974 | Rollins |
| 4,134,395 A | 1/1979 | Davis |
| 4,889,526 A | 12/1989 | Rauscher et al. |
| 5,207,223 A | 5/1993 | Adler |
| 5,267,938 A | 12/1993 | Konotchick |
| 5,427,097 A | 6/1995 | Depp |
| 5,441,495 A | 8/1995 | Liboff et al. |
| 5,531,227 A | 7/1996 | Schneider |
| 5,707,334 A | 1/1998 | Young |
| 5,738,625 A | 4/1998 | Gluck |
| 5,766,124 A | 6/1998 | Polson |
| 5,891,034 A | 4/1999 | Bucholz |
| 6,042,531 A | 3/2000 | Holcomb |
| 6,132,361 A | 10/2000 | Epstein et al. |
| 6,132,631 A | 10/2000 | Nallan et al. |
| 6,149,577 A | 11/2000 | Bouldin et al. |
| 6,179,770 B1 | 1/2001 | Mould |
| 6,179,771 B1 | 1/2001 | Mueller |
| 6,198,958 B1 | 3/2001 | Ives et al. |
| 6,236,875 B1 | 5/2001 | Bucholz et al. |
| 6,266,556 B1 | 7/2001 | Ives et al. |
| 6,351,573 B1 | 2/2002 | Schneider |
| 6,356,781 B1 | 3/2002 | Lee et al. |
| 6,425,852 B1 | 7/2002 | Epstein et al. |
| 6,447,440 B1 | 9/2002 | Markoll |
| 6,461,289 B1 | 10/2002 | Muntermann |
| 6,488,617 B1 | 12/2002 | Katz |
| 6,507,751 B2 | 1/2003 | Blume et al. |
| 6,537,197 B1 | 3/2003 | Ruohonen et al. |
| 6,571,123 B2 | 5/2003 | Ives et al. |
| 6,572,528 B2 | 6/2003 | Rohan et al. |
| 6,663,556 B2 | 12/2003 | Barker |
| 6,818,669 B2 | 11/2004 | Moskowitz et al. |
| 6,849,040 B2 | 2/2005 | Ruohonen et al. |
| 6,858,000 B1 | 2/2005 | Schukin et al. |
| 6,972,097 B2 | 12/2005 | Yoshida et al. |
| 7,023,311 B2 | 4/2006 | Baldwin et al. |
| 7,087,008 B2 | 8/2006 | Fox et al. |
| 7,088,210 B2 | 8/2006 | Day et al. |
| 7,104,947 B2 | 9/2006 | Riehl |
| 7,141,028 B2 | 11/2006 | McNew |
| 7,153,256 B2 | 12/2006 | Riehl |
| 7,155,284 B1 | 12/2006 | Whitehurst et al. |
| 7,236,830 B2 | 6/2007 | Gliner |
| 7,239,910 B2 | 7/2007 | Tanner |
| 7,367,935 B2 | 5/2008 | Mechlenburg et al. |
| 7,367,936 B2 | 5/2008 | Myers et al. |
| 7,396,326 B2 | 7/2008 | Ghiron et al. |
| 7,483,747 B2 | 1/2009 | Gliner et al. |
| 7,520,848 B2 | 4/2009 | Schneider et al. |
| 7,771,341 B2 | 8/2010 | Rogers |
| 7,856,264 B2 | 12/2010 | Firlik et al. |
| 7,904,134 B2 | 3/2011 | McIntyre et al. |
| 8,052,591 B2 | 11/2011 | Mishelevich |

(Continued)

FOREIGN PATENT DOCUMENTS

| | | |
|---|---|---|
| DE | 10242542 A1 | 4/2004 |
| EP | 0501048 A1 | 9/1992 |

(Continued)

OTHER PUBLICATIONS

Dantec magnetic stimulation product information on MagPro X100 with MagOption; http://www.danica.nl/neuro/neuro-magnetische-stimulatoren.htm; Jan. 15, 2009.

(Continued)

*Primary Examiner* — John Lacyk
(74) *Attorney, Agent, or Firm* — Shay Glenn LLP

(57) ABSTRACT

Systems and methods for modulating deep brain target regions using an array of TMS electromagnets, wherein each TMS electromagnet stimulates the target at a level that is below motor threshold (MT). Neurological disorders (or disorders having neurological effects) may be treated by sub-MT stimulation of deep-brain targets from an array of TMS electromagnets.

16 Claims, 8 Drawing Sheets

(56) References Cited

U.S. PATENT DOCUMENTS

| | | | |
|---|---|---|---|
| 8,267,850 B2* | 9/2012 | Schneider et al. ............ 600/14 |
| 2002/0022777 A1 | 2/2002 | Crieghton et al. |
| 2002/0097125 A1 | 7/2002 | Davey |
| 2003/0004392 A1 | 1/2003 | Tanner et al. |
| 2003/0028072 A1 | 2/2003 | Fischell et al. |
| 2003/0065243 A1 | 4/2003 | Tanner |
| 2003/0204135 A1 | 10/2003 | Bystritsky |
| 2004/0010177 A1 | 1/2004 | Rohan et al. |
| 2004/0077921 A1 | 4/2004 | Becker et al. |
| 2004/0078056 A1 | 4/2004 | Zangen et al. |
| 2004/0193000 A1 | 9/2004 | Riehl |
| 2004/0193002 A1 | 9/2004 | Tanner et al. |
| 2004/0204625 A1* | 10/2004 | Riehl et al. ................. 600/9 |
| 2005/0033154 A1 | 2/2005 | deCharms |
| 2005/0038313 A1 | 2/2005 | Ardizzone |
| 2005/0046532 A1 | 3/2005 | Dodd |
| 2005/0107655 A1 | 5/2005 | Holzner |
| 2005/0113630 A1 | 5/2005 | Fox et al. |
| 2005/0124848 A1 | 6/2005 | Holzner |
| 2005/0148808 A1 | 7/2005 | Cameron et al. |
| 2005/0154426 A1 | 7/2005 | Boveja et al. |
| 2005/0222625 A1 | 10/2005 | Laniado et al. |
| 2005/0234286 A1 | 10/2005 | Riehl et al. |
| 2005/0256539 A1 | 11/2005 | George et al. |
| 2006/0058853 A1 | 3/2006 | Bentwich |
| 2006/0094924 A1 | 5/2006 | Riehl et al. |
| 2006/0106430 A1 | 5/2006 | Fowler et al. |
| 2006/0122454 A1 | 6/2006 | Riehl et al. |
| 2006/0122496 A1 | 6/2006 | George et al. |
| 2006/0149337 A1 | 7/2006 | John |
| 2006/0173274 A1 | 8/2006 | George et al. |
| 2006/0189866 A1 | 8/2006 | Thomas et al. |
| 2006/0199992 A1 | 9/2006 | Eisenberg et al. |
| 2006/0218790 A1 | 10/2006 | Day et al. |
| 2006/0287566 A1 | 12/2006 | Zangen et al. |
| 2007/0027353 A1 | 2/2007 | Ghiron et al. |
| 2007/0027504 A1 | 2/2007 | Barrett et al. |
| 2007/0083074 A1 | 4/2007 | Sotiriou |
| 2007/0100392 A1 | 5/2007 | Maschino et al. |
| 2007/0100398 A1 | 5/2007 | Sloan |
| 2007/0242406 A1 | 10/2007 | Annis et al. |
| 2007/0265489 A1 | 11/2007 | Fowler et al. |
| 2007/0293916 A1 | 12/2007 | Peterchev |
| 2008/0033297 A1 | 2/2008 | Sliwa |
| 2008/0058582 A1 | 3/2008 | Aho et al. |
| 2008/0064950 A1 | 3/2008 | Ruohonen et al. |
| 2008/0123922 A1 | 5/2008 | Gielen et al. |
| 2008/0161636 A1 | 7/2008 | Hurme et al. |
| 2008/0306326 A1 | 12/2008 | Epstein |
| 2009/0018384 A1 | 1/2009 | Boyden et al. |
| 2009/0024021 A1 | 1/2009 | George et al. |
| 2009/0099405 A1 | 4/2009 | Schneider et al. |
| 2009/0099623 A1 | 4/2009 | Bentwich |
| 2009/0112133 A1 | 4/2009 | Deisseroth et al. |
| 2009/0112277 A1 | 4/2009 | Wingeier et al. |
| 2009/0114849 A1 | 5/2009 | Schneider et al. |
| 2009/0124848 A1 | 5/2009 | Miazga |
| 2009/0156884 A1 | 6/2009 | Schneider et al. |
| 2009/0187062 A1 | 7/2009 | Saitoh |
| 2009/0189470 A1 | 7/2009 | McClellan |
| 2009/0227830 A1 | 9/2009 | Pillutla et al. |
| 2009/0234243 A1 | 9/2009 | Schneider et al. |
| 2010/0004500 A1 | 1/2010 | Gliner et al. |
| 2010/0185042 A1 | 7/2010 | Schneider et al. |
| 2010/0256436 A1 | 10/2010 | Partsch et al. |
| 2010/0256438 A1 | 10/2010 | Mishelevich et al. |
| 2010/0256439 A1 | 10/2010 | Schneider et al. |
| 2010/0298623 A1 | 11/2010 | Mishelevich et al. |
| 2010/0331602 A1 | 12/2010 | Mishelevich et al. |
| 2011/0004450 A1 | 1/2011 | Mishelevich et al. |
| 2011/0082326 A1 | 4/2011 | Mishelevich et al. |
| 2011/0273251 A1 | 11/2011 | Mishelevich et al. |
| 2012/0016177 A1 | 1/2012 | Mishelevich et al. |
| 2012/0310035 A1 | 12/2012 | Schneider et al. |
| 2013/0096363 A1 | 4/2013 | Schneider et al. |
| 2013/0204330 A1 | 8/2013 | Schneider et al. |

FOREIGN PATENT DOCUMENTS

| | | |
|---|---|---|
| EP | 0709115 A1 | 5/1996 |
| EP | 0788813 A1 | 8/1997 |
| EP | 1326681 B1 | 1/2007 |
| GB | 2271931 A | 5/1994 |
| GB | 2336544 A | 10/1999 |
| JP | 64-046479 | 2/1989 |
| JP | 5-237197 | 9/1993 |
| JP | 2003-180649 | 7/2003 |
| JP | 2003-205040 | 7/2003 |
| KR | 10-0457104 | 11/2004 |
| WO | WO 98/56302 A1 | 12/1998 |
| WO | WO 99/39769 A1 | 8/1999 |
| WO | WO 99/55421 A2 | 11/1999 |
| WO | WO 00/74777 A1 | 12/2000 |
| WO | WO 00/78267 A2 | 12/2000 |
| WO | WO 02/09811 A1 | 2/2002 |
| WO | WO 02/32504 A2 | 4/2002 |
| WO | WO 03/082405 A1 | 10/2003 |
| WO | WO 2004/087255 A1 | 10/2004 |
| WO | WO 2005/000153 A2 | 1/2005 |
| WO | WO 2006/124914 A2 | 11/2006 |
| WO | WO 2007/050592 A2 | 5/2007 |
| WO | WO 2007/130308 A2 | 11/2007 |
| WO | WO 2009/042863 A1 | 4/2009 |

OTHER PUBLICATIONS

Ruohonen, J.; Transcranial magnetic stimulation: modelling and new techniques; (doctoral dissertation); Helsinki Univ. of Tech.; Dept. of Eng. Physics and Mathematics; Espoo, Finland; Dec. 1998.

Agnew et al.; Considerations for safety in the use of extracranial stimulation for motor evoked potentials; Neurosurgery; vol. 20; pp. 143-147; Jan. 1987.

Avery et al.; A Controlled Study of Repetitive Transcranial Magnetic Stimulation in Medication-Resistant Major Depression; Biological Psychiatry; vol. 59; pp. 187-194; Jul. 2005.

Barker et al.; Non invasive magnetic stimulation of the human motor cortex; Lancet; vol. 1; pp. 1106-1110; May 1985.

Barker, A. T.; An introduction to the basic principles of magnetic nerve stimulation; Journal of Clinical Neurophysiology; vol. 8; No. 1; pp. 26-37; Jan. 1991.

Basser et al.; Stimulation of myelinated nerve axon by electromagnetic induction; Medical & Biological Engineering and Computing.; vol. 29; pp. 261-268; May 1991.

Bohning et al.; Mapping transcranial magnetic stimulation (TMS) fields in vivo with MRI; NeuroReport; vol. 8; No. 11; pp. 2535-2538; Jul. 28, 1997.

Conca et al.; Effect of chronic repetitive transcranial magnetic stimulation on regional cerebral blood flow and regional cerebral glucose uptake in drug treatment-resistant depressives. A brief report; Neuropsychobiology; vol. 45; No. 1; pp. 27-31; (Month Unavailable) 2002.

Davey et al.; Designing transcranial magnetic stimulation systems; IEEE Transactions on Magnetics; vol. 41; No. 3; pp. 1142-1148; Mar. 2005.

Davey et al.; Modeling the effects of electrical conductivity of the head on the induced electrical field in the brain during magnetic stimulation; Clinical Neurophysiology; vol. 114; pp. 2204-2209; Jun. 2003.

Davey et al.; Prediction of magnetically induced electric fields in biologic tissue; IEEE Transactions on Biomedical Engineering; vol. 38; pp. 418-422; May 1991.

Davey et al.; Suppressing the surface field during transcranial magnetic stimulation; IEEE Transactions on Biomedical Engineering; vol. 53; No. 2; Feb. 2006; pp. 190-194.

DeRidder et al.; Transcranial magnetic stimulation for tinnitus: influence of tinnitus duration on stimulation parameter choice and maximal tinnitus suppression; Otol Neurotol.; vol. 26; No. 4; pp. 616-619; Jul. 2005.

(56) References Cited

OTHER PUBLICATIONS

Epstein et al.; Magnetic coil suppression of visual perception at an extracalcarine site; J. Clin. Neurophysiol; vol. 13; No. 3; pp. 247-252; May 1996.

George, Mark S.; Stimulating the brain; Scientific American; Sep. 2002; pp. 67-73.

Han et al.; Multichannel magnetic stimulation system design considering mutual couplings among the stimulation coils; IEEE Trans. on Biomedical Engineering; vol. 51; No. 5; pp. 812-817; May 2004.

Hayward et al.; The role of the anterior cingulate cortex in the counting stroop task; Exp Brain Res; vol. 154(3); pp. 355-358; Feb. 2004.

Hemond et al.; Transcranial magnetic stimulation in neurology: What we have learned from randomized controlled studies; Neuromodulation: Technology at the Neural Interface; vol. 10; No. 4; pp. 333-344; 2007.

Hovey, C. et al.; The new guide to magnetic stimulation; The Magstim Company Ltd.; Carmathenshire, United Kingdom; Oct. 2003; 42 pages.

Hsu et al., Analysis of Efficiency of Magnetic Stimulation; IEEE Transactions on Biomedical Engineering; vol. 50. No. 11; Sep. 2003; pp. 1276-1285.

Huang et al.; Theta Burst Stimulation of the Human Motor Cortex; Neuron; vol. 45; pp. 201-206; Jan. 2005.

Isenberg et al.; Low frequency rTMS stimulation of the right frontal cortex is as effective as high frequency rTMS stimulation of the left frontal cortex for antidepressant-free, treatment-resistant depressed patients; Ann Clin Psychiatry; vol. 17; No. 3; pp. 153-159; Jul.-Sep. 2005.

Kamitani et al.; A model of magnetic stimulation of neocortical neurons; Neurocomputing; vol. 38; No. 40; Jun. 2001; pp. 697-703.

Kandel et al.; Chapter 12: Synaptic Integration; Principles of Neural Science; Editors: Kandel, Schwartz and Jessell; 4th Edition, McGraw-Hill; pp. 208-227; Jan. 5, 2000.

Lang et al.; How does transcranial DC stimulation of the primary motor cortex alter regional neuronal activity in the human brain?; Eur. J. Neurosci.; vol. 22; No. 2; pp. 495-504; Jul. 2005.

Lefaucheur, Jean-Pascal; Use of repetitive transcranial magnetic stimulation in pain relief; Expert Rev Neurother; vol. 8, No. 5: pp. 799-808; May 2008.

Lefaucheur et al.; Pain relief induced by repetitive transcranial magnetic stimulation of precentral cortex; Neuroreport; vol. 12, issue 13: pp. 2963-2965; Sep. 17, 2001.

Lefaucheur et al.; Somatotopic organization of the analgesic effects of motor cortex rTMS in neuropathic pain; Neurology; vol. 67, No. 11: pp. 1998-2004; Dec. 12, 2006.

Levkovitz et al.; A randomized controlled feasibility and safety study of deep transcranial magnetic stimulation; Clin. Neurophysiol.; vol. 118(12); pp. 2730-2744; Dec. 2007.

Lin et al.; Magnetic coil design considerations for functional magnetic stimulation; IEEE Trans. on Biomedical Eng.; vol. 47; No. 5; pp. 600-610; May 2000.

Magstim Website: http://www.magstim.com/magneticstimulators/magstimacc/12494.html (printed Mar. 23, 2010).

Martin et al.; Transcranial magnetic stimulation for treating depression; Cochrane Review; (Month Unavailable) 2002 (In (eds.): The Cochrane Library. Oxford: Update Software: The Cochrane Library. Oxford: Update Software.).

Mayberg et al.; Deep brain stimulation for treatment-resistant depression; Neuron; vol. 45; pp. 651-660; Mar. 2005.

Miranda et al.; The Electric Field Induced in the Brain by Magnetic Stimulation: A 3-D Finite-Element Analysis of the Effects of Tissue Heterogeneity and Anisotropy; IEEE Transactions on Biomedical Engineering; vol. 50; No. 9; Sep. 2003; pp. 1074-1085.

Nadeem et al.; Computation of electric and magnetic stimulation in human head using the 3-D impedance method; IEEE Trans on Biomedical Eng; vol. 50; No. 7; pp. 900-907; Jul. 2003.

Ohnishi et al.; rCBF changes elicited by rTMS over DLPFC in humans; Suppl Clin Neurophysiol.; vol. 57: pp. 715-720; (Month Unavailable) 2004.

Paton et al.; Vascular-brain signaling in hypertension: role of angiotensin II and nitric oxide; Curr. Hypertens Rep; vol. 9; No. 3; pp. 242-247; Jun. 2007.

Rossini et al.; Transcranial magnetic stimulation: Diagnostic, therapeutic, and researchpotential; Neurology; vol. 68, No. 7: pp. 484-488; Feb. 13, 2007.

Roth et al.; A coil design for transcranial magnetic stimulation of adeep brain regions; J. Clin. Neurophysiology; vol. 19; No. 4; Aug. 2002; pp. 361-370.

Ruohonen et al.; Theory of Multichannel Magnetic Stimulation: Toward Functional Neuromuscular Rehabilitation; IEEE Transactions on Biomedical Engineering; vol. 46; No. 6; pp. 646-651; Jun. 1999.

Ruohonen et al.; (Chapter 2); Magnetic stimulation in clinical neurophysiology; Second Ed.; Ed. Elsevier Inc.; pp. 17-30; (Month Unavailable) 2005.

Ruohonen et al.; Focusing and targeting of magnetic brain stimulation using multiple coils; Medical & Biological Engineering and Computing; vol. 35; pp. 297-301; May 1998.

Sackheim, H. A.; Commentary: Magnetic stimulation therapy and ECT; Convulsive Therapy; vol. 10; No. 4; Dec. 1994; pp. 255-285.

Sekino et al.; Comparison of current distributions in electroconvulsive therapy and transcranial magnetic stimulation; J. of Applied Physics; vol. 91; No. 10; pp. 8730-8732; May 15, 2002.

Speer et al.; Opposite effects of high and low frequency rTMS on regional brain activity in depressed patients; Biol. Psychiatry; vol. 48; No. 12; pp. 1133-1141; Dec. 15, 2000.

Takano et al.; Short-term modulation of regional excitability and blood flow in human motor cortex following rapid-rate transcranial magnetic stimulation; Neuroimage; vol. 23; No. 3; pp. 849-859; Nov. 2004.

Traad, Monique; A Quantitative Positioning Device for Transcranial Magnetic Stimulation; Engineering in Medicine and Biology Society; 1990; Proceedings of the 12th Annual Int'l Conf. of the IEEE; Philadelphia, PA; p. 2246; Nov. 1-4, 1990.

Ueno et al.; Localized stimulation of neural tissues in the brain by means of a paired configuration of time-varying magnetic fields; J. Appl. Phys.; vol. 64; No. 10; pp. 5862-5864; Nov. 15, 1988.

Vayssettes-Courchay et al.; Role of the nucleus tractus solitarii and the rostral depressive area in the sympatholytic effect of 8-hydroxy-2-(di-n-propylamino)tetralin in the cat; Eur. J. Pharmacol.; vol. 242; No. 1; pp. 37-45; Sep. 21, 1993.

Wagner et al.; Three-dimensional head model simulation of transcranial magnetic stimulation; IEEE Trans. on Biomedical Engineering; vol. 51; No. 9; pp. 1586-1598; Sep. 2004.

Wagner et al.; Transcranial direct current stimulation: A computer-based human model study; NeuroImage; vol. 35; issue 3; Apr. 15, 2007; pp. 1113-1124.

Waki et al.; Junctional adhesion molecule-1 is upregulated in spontaneously hypertensive rats: evidence for a prohypertensive role within the brain stem; Hypertension; vol. 49; No. 6; pp. 1321-1327; Jun. 2007.

Wasserman et al.; Therapeutic application of repetitive magnetic stimulation: a review; Clinical Neurophysiology; vol. 112; pp. 1367-1377; Apr. 2001.

Wasserman, E. M.; Risk and safety of repetitive transcranial magnetic stimulation: report and suggested guidelines from the International Workshop on the Safety of Repetitive Transcranial Magnetic Stimulation, Jun. 5-7, 1996; Electro-encephalography and Clinical Neurophysiology; vol. 108; pp. 1-16; Jan. 1998.

Xiao et al.; Magnetic Nanocomposite Paste: An Ideal High-$\mu$, k and Q Nanomaterial for Embedded Inductors in High Frequency Electronic Appls.; Proceedings of the 9th World Multiconference on Systemics, Cybernetics and Informatics; Orlando, FL; Jul. 10-13, 2005.

Yang et al.; 3D Realistic Head Model Simulation Based on Transcranial Magnetic Stimulation; Conf Proc IEEE Eng Med Biol Soc.; vol. Suppl.; Aug. 30-Sep. 3, 2006; 4 pages.

Yu et al.; Pathogenesis of normal-appearing white matter damage in neuromyelitis optica: diffusion-tensor MR imaging; Radiology; vol. 246, No. 1: pp. 222-228; Jan. 2008.

(56) References Cited

OTHER PUBLICATIONS

Mishelevich et al.; U.S. Appl. No. 12/680,912 "Transcranial magnetic stimulation with protection of magnet-adjacent structures," filed Mar. 31, 2010.
Schneider et al.; U.S. Appl. No. 12/838,299 entitled "Transcranial magnetic stimulation field shaping," filed Jul. 16, 2010.
Mishelevich et al.; U.S. Appl. No. 12/990,235 entitled "Transcranial magnetic stimulation by enhanced magnetic field perturbations," filed Oct. 29, 2010.
Schneider, M. Bret.; U.S. Appl. No. 13/169,967 entitled "Enhanced Spatial Summation for Deep-Brain Transcranial Magnetic Stimulation," filed Jun. 27, 2011.
Sadler, John W.; U.S. Appl. No. 13/512,496 entitled "Power Management in Transcranial Magnetic Stimulators," filed May 29, 2012.
Aleman et al.; Efficacy of slow repetitive transcranial magnetic stimulation in the treatment of resistant auditory hallucinations in schizophrenia: a meta-analysis; J Clin Psychiatry; 68(3):416-21; Mar. 2007.
Alonso et al.; Right prefrontal repetitive transcranial magnetic stimulation in obsessive-compulsive disorder: a double-blind, placebo-controlled study; Am J Psychiatry; 158(7):1143-5; Jul. 2001.
Antal et al.; Transcranial Direct Current Stimulation Over Somatosensory Cortex Decreases Experimentally Induced Acute Pain Perception; Clin J Pain; vol. 24, No. 1; pp. 56-63; Jan. 2008.
Bikson et al.; Transcranial Direct Current Stimulation for Major Depression: A General System for Quantifying Transcranial Electrotherapy Dosage; Current Treatment Options in Neurology; 10(5):377-385; Sep. 2008.
Blount et al.; The Influence of Thyroid and Thiouracil on Mice Exposed to Roentgen Radiation; Science; 109(2822); pp. 83-84; Jan. 28, 1949.
Bodo et al.; The role of multidrug transporters in drug availability, metabolism and toxicity; Toxicol Lett; pp. 140-141; Review; pp. 133-143; Apr. 11, 2003.
Boggioa et al.; A randomized, double-blind clinical trial on the efficacy of cortical direct current stimulation for the treatment of major depression; International Journal of Neuropsychopharmacology; 11(2): 249-254; Mar. 2008.
Buxton; Pharmacokinetics and Phamacodynamics; Goodman & Gilman's The Pharmacological Basis of Therapeutics (11th Ed.); McGraw-Hill, ©2006; pp. 1-23; pub. date Oct. 28, 2005.
Cohen et al.; Repetitive transcranial magnetic stimulation of the right dorsolateral prefrontal cortex in posttraumatic stress disorder: a double-blind, placebo-controlled study; Am J Psychiatry; 161(3):515-24; Mar. 2004.
Fecteau et al.; Diminishing risk-taking behavior by modulating activity in the prefrontal cortex: a direct current stimulation study; J Neurosci.; 27(46):12500-5; Nov. 14, 2007.
Fitzgerald et al.; Transcranial magnetic stimulation in the treatment of depression: a double-blind, placebo-controlled trial; Arch Gen Psychiatry; 60(10):1002-8; Oct. 2003.
Fregni et al.; Anodal transcranial direct current stimulation of prefrontal cortex enhances working memory; Exp Brain Res.; 166(1); pp. 23-30; Sep. 2005.
George et al.; Prefrontal Repetitive Transcranial Magnetic stimulation (rTMS) Changes Relative Perfusion Locally and Remotely; Human Psychopharmacol Clin Exp; 14(3); pp. 161-170; Apr. 1999.
Khedr et al.; Therapeutic effect of repetitive transcranial magnetic stimulation on motor function in Parkinson's disease patients; Eur J Neurol; 10(5):567-72; Sep. 2003.
Kimeldorf et al.; The effect of exercise upon the lethality of roentgen rays for rats; Science; 112(2902); pp. 175-6; Aug. 1950.
Kleinjung et al.; Transcranial magnetic stimulation: a new diagnostic and therapeutic tool for tinnitus patients; Int Tinnitus J.; 14(2):112-8; Jul./Dec. 2008.
Lang et al.; Bidirectional Modulation of Primary Visual Cortex Excitability: A Combined tDCS and rTMS Study; Investigative Ophthalmology and Visual Science; 48(12): 5782-5787; Dec. 2007.
Lang et al.; Preconditioning with Transcranial Direct Current Stimulation Sensitizes the Motor Cortex to Rapid-Rate Transcranial Magnetic Stimulation and Controls the Direction of After-Effects; Biol. Psychiatry; 56(9): 634-639; Nov. 1, 2004.
Lemaire et al.; Influence of blood components on the tissue uptake indices of cyclosporin in rats; J Pharmacol Exp Ther; 244(2); pp. 740-3; Feb. 1988.
Mansur et al.; A sham stimulation-controlled trial of rTMS of the unaffected hemisphere in stroke patients; Neurology; 64(10):1802-4; May 24, 2005.
Nitsche et al.; Excitability changes induced in the human motor cortex by weak transcranial direct current stimulation; Journal of Physiology; 527(3):633-639; Sep. 15, 2000.
O'Reardon et al.; Efficacy and safety of transcranial magnetic stimulation in the acute treatment of major depression: a multisite randomized controlled trial; Biol Psychiatry; 62(11):1208-16; Dec. 1, 2007.
Ragert et al.; Improvement of spatial tactile acuity by transcranial direct current stimulation; Clin. Neurophysiol.; 119(4):805-11; Apr. 2008 (author manuscript).
Roizen Blatt et al.; Site-specific Effects of Transcranial Direct Current Stimulation on Sleep and Pain in Fibromyalgia: A Randomized, Sham-controlled study; Pain Practice; 7(4): 297-306; Dec. 7, 2007.
Rubin et al.; Radiosensitivity and radioresistance of tumors; Clinical Radiation Pathology; WB Saunders; Ch. 24, pp. 894-933; Jun. 1968.
Rubin et al.; The Modification of Radiation Response; Clinical Radiation Pathology; WB Saunders; Ch. 26, pp. 973-1008; Jun. 1968.
Smith et al.; Effect of thyroid hormone on radiation lethality; Am J Physiol; 165 (3); pp. 639-650; Jun. 1951.
Sparing et al.; Enhancing language performance with non-invasive brain stimulation R A transcranial direct current stimulation study in healthy humans; Neuropsychologia; 46(1): 261-268; Jan. 15, 2008.
Theodore et al.; Transcranial magnetic stimulation for the treatment of seizures: a controlled study; Neurology; 59(4):560-2; Aug. 27, 2002.
Ueno; Individual differences in radio sensitivity of mice correlated with their metabolic rate; Acta Radiol Ther Phys Biol; 10(4); pp. 427-432; Aug. 1971.
Wasan et al.; Lipid transfer protein I facilitated transfer of cyclosporine from low- to high-density lipoproteins is only partially dependent on its cholesteryl ester transfer activity; J Pharmacol Exp Ther; 284 (2); pp. 599-605; Feb. 1998.
Zanette et al.; The effect of repetitive transcranial magnetic stimulation on motor performance, fatigue and quality of life in amyotrophic lateral sclerosis; J Neurol Sci.; 270(1-2):18-22; Jul. 15, 2008.
Zheng et al. High-frequency rTMS Treatment Increases Left Prefrontal Myo-Inositol in Young Patients with Treatment-Resistant Depression; Prog Neuropsychopharmacol Biol Psychiatry; 34(7); pp. 1189-1195; Oct. 1, 2010.
Schneider et al.; U.S. Appl. No. 13/877,428 entitled "Transverse transcranial magnetic stimulation coil placement for improved analgesia," filed Jun. 27, 2013.
Schneider et al.; U.S. Appl. No. 13/888,263 entitled "Transverse transcranial magnetic stimulation for improved analgesia," filed May 6, 2013.

\* cited by examiner

FIG. 2A    FIG. 2B    FIG. 2C
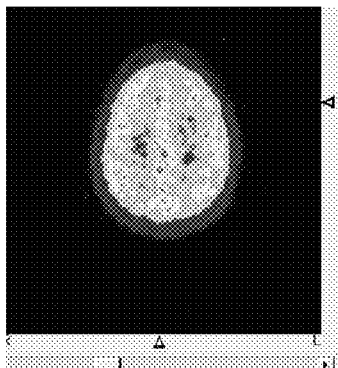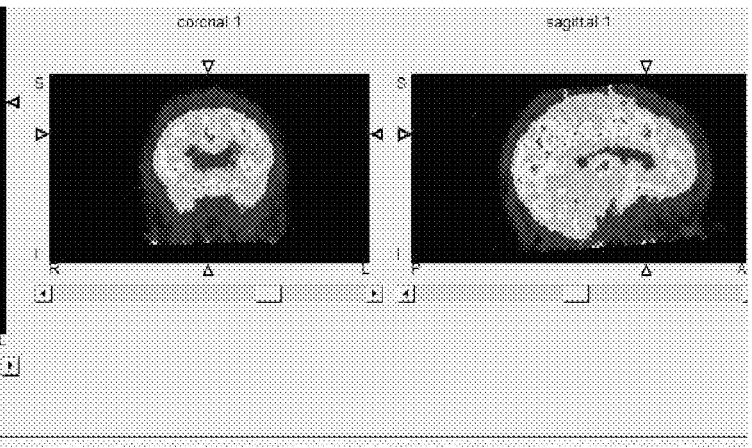
FIG. 2D    FIG. 2E    FIG. 2F
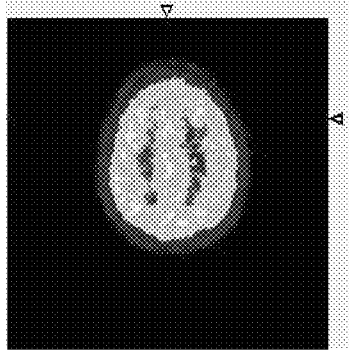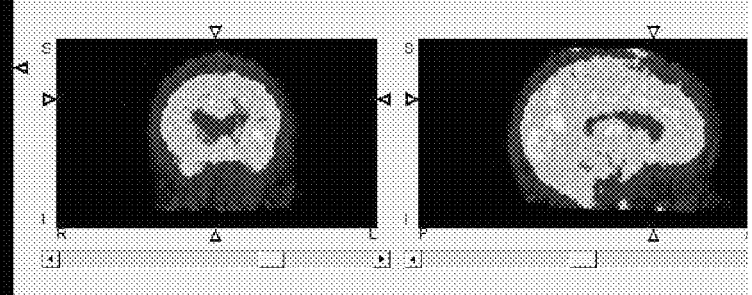

FIG. 3A

SUBJECT #1      MT=80%

|        | Front | Pt Left | Pt Right | Top/Central |
|--------|-------|---------|----------|-------------|
| Stim # | 4     | 3       | 2        | 1           |
| 1159   | 50    | 20      | 20       | 50          |
| 1209   | 55    | 25      | 25       | 55          |
| 1214   | 60    | 30      | 30       | 60          |
| 1217   | 70    | 30      | 30       | 70          |
| 1218   | 65    | 30      | 30       | 65          |
| 1224   | 60    | 30      | 30       | 60          |
| 1226   | 65    | 30      | 30       | 65          |
| 1229   | END   |         |          |             |

FIG. 3B

SUBJECT #2      MT=85%

|         | Front | Pt Left | Pt Right | Top/Central |
|---------|-------|---------|----------|-------------|
| Stim. # | 4     | 3       | 2        | 1           |
| 1615    | 50    | 20      | 20       | 50          |
|         | 55    | 20      | 20       | 55          |
|         | 55    | 25      | 25       | 55          |
|         | 60    | 25      | 25       | 60          |
|         | 60    | 20      | 20       | 60          |
|         | 60    | 25      | 25       | 60          |
|         | 65    | 25      | 25       | 65          |
|         | 65    | 30      | 30       | 65          |
|         | 60    | 30      | 30       | 60          |
|         | 65    | 30      | 30       | 65          |
| 1627    | 70    | 35      | 35       | 70          |
|         | 70    | 35      | 35       | 80          |
|         | 70    | 40      | 40       | 80          |
|         | 70    | 40      | 40       | 75          |
|         | 70    | 40      | 40       | 75          |
| 1652    | END   |         |          |             |

SUB-MOTOR-THRESHOLD STIMULATION OF DEEP BRAIN TARGETS USING TRANSCRANIAL MAGNETIC STIMULATION

CROSS REFERENCE TO RELATED APPLICATIONS

This patent application claims priority to provisional patent application Ser. No. 61/254,964, filed on Oct. 26, 2009, titled "SUB-MOTOR-THRESHOLD STIMULATION OF DEEP BRAIN TARGETS USING TRANSCRANIAL MAGNETIC STIMULATION," which is herein incorporated by reference in its entirety.

This patent application may be related to pending PCT application PCT/2008/073751, filed on Aug. 20, 2008, which claims priority to U.S. Provisional Patent Application Ser. No. 60/956,920, filed on Aug. 20, 2007, U.S. Provisional Patent Application Ser. No. 60/970,958, filed on Sep. 9, 2007, and U.S. Provisional Patent Application Ser. No. 61/077,488, filed on Jul. 2, 2008. This patent application may also be related to PCT application PCT/US2008/075575 (WO 2009/033144), filed on Sep. 8, 2008, which claims priority to U.S. Provisional Patent Application Ser. Nos. 60/970,534, filed Sep. 7, 2007; 60/970,532, filed Sep. 7, 2007; and 60/975,177, filed Sep. 26, 2007. This patent application may also be related to pending U.S. patent application Ser. No. 12/185,554, filed Aug. 4, 2008, which claims priority to U.S. Provisional Patent Application Ser. No. 60/954,018, field on Aug. 5, 2007. This patent application may also be related to pending U.S. patent application Ser. No. 12/324,227, filed Nov. 26, 2008, which claims priority to U.S. Provisional Patent Application Ser. No. 60/990,300, filed Nov. 27, 2007; and U.S. Provisional Patent Application Ser. No. 60/992,385, filed Dec. 5, 2007. Each of these patent applications is herein incorporated by reference in its entirety.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD OF THE INVENTION

Described herein are systems and methods for Transcranial Magnetic Stimulation (TMS) including one or more TMS electromagnets for stimulation of target deep brain regions to stimulate, enhance neural activity or inhibit neural activity.

BACKGROUND OF THE INVENTION

Deep brain stimulation using non-invasive techniques has long been a goal for therapeutic treatment of numerous disorders. As understood by those of skill in the art, deep brain regions, typically include those regions of the brain that are deeper into the brain that the outer cortical region of the brain, and particularly the region that is separated from the outer surface of the brain closest to the skull. In this context, deep brain regions may include, for example, the cingulate gyms and insula, thalamus, subthalamic nucleus, and globus pallidus.

It is widely believed in the field of Transcranial Magnetic Stimulation that the stimulation of deep brain target regions will require an increased level of stimulation because the magnetic flux falls off as a function of distance according to known principles. Thus, it is through that to effectively elicit firing of neurons from these deep brain structures, typically considered as triggering an action potential in the neural structure of the deep brain target, adequate stimulation must be received at the deep brain target; otherwise threshold for generating an action potential will not be achieved. The same principles may apply to the stimulation of neurons to hyperpolarize (inhibiting action potentials) or depolarize (making neurons more excitable). The threshold for stimulation of neurons (including deep brain targets) has historically been the motor threshold, which is the power required to activate an electromagnet coil to produce a motor response in a limb opposite the side of the motor cortex that is being stimulated by the coils (applied through the scalp and skull).

In the context of the present invention, typical deep brain target regions may include, for example, the insula and the cingulate gyms. Stimulation of a target deep brain regions without stimulating or depressing stimulation of nearby non-target brain region, and particularly brain regions between the target deep brain region and the TMS electromagnet, has previously been achieved by optimizing the power applied to the TMS electromagnet(s) so that the electromagnetic field(s) reaching the target and causing the fields to summate by one or more means including magnetic field overlap/superposition (physical summation), temporal summation, and spatial summation) to achieve the desired stimulation. Optimization typically means minimizing the power applied and using the best coil orientations and locations for delivery of each pulse from a TMS electromagnet so that the intervening non-target regions are not stimulated to the extent that non-intended effects either do not occur or are minimized.

Thus, power applied to any given electromagnet, and/or the rate that the power is applied, is preferably limited. However, the power applied by one or more TMS electromagnets intended to stimulate a deep brain target such as the insula or cingulate gyms must be sufficient to activate the deep brain target. While limiting the power and frequency applied to a target from a single stimulating location may protect structures superficial to the deeper target, it may be impossible to effectively stimulate a deep target because of the rapid fall off of the magnetic field. The attenuation of the magnetic field is commonly believed to be equivalent to roughly $1/(distance)^2$ at short distances This inverse-square relationship is particularly significant, because a version of this relationship has been used to determine the strength needed for stimulation of a deep brain target region by one or more TMS electromagnets. Known deep-brain stimulation techniques, including those described by Mishelevich and Schneider, have generally applied the inverse-square relationship to determine the stimulation power and/or frequency to be applied. As a result, the power predicted as necessary to stimulate structures further from the TMS coil (such as deep brain targets) has been widely held to be relatively large, particularly in light of the expectation that effective stimulation is achieved only when exceeding a threshold such as the motor threshold.

Herein we describe a system comprising an array of electromagnets configured to modulate activity of a deep-brain target when all of the TMS electromagnets in the system are operating at levels such that the summation at the target is below the motor threshold.

SUMMARY OF THE INVENTION

Described herein are systems and method for modulating deep brain target regions using an array of TMS electromagnets, wherein each TMS electromagnet stimulates the target at a level that is below motor threshold (MT). For example, the level may be less than 100% MT, less than 90% MT, less than 80% MT, less than 70% MT, less than 60% MT, etc. The level of stimulation for each magnet of the array may be independently or collectively controlled, but in general, the level of stimulation at the target is less than MT for all of the TMS electromagnets in the array. For example, the stimulation applied to each TMS coil in an array may be below MT for that coil, which may be determined by using the coil positioned above a motor cortex region of the brain to determine the level at which a motor response is elicited. The power applied by each TMS electromagnet may be below the MT for that TMS electromagnet; in addition, the power seen at the deep brain target may be below the MT.

In general, the sub-MT stimulation described here is unexpectedly effective, despite being sub-MT at the deep-brain target. The stimulation seen at more cortical regions (between the deep brain target and the TMS magnet) may be either sub-MT or at or above MT, unless the superficial cortex is one of the targets in addition to the deep-brain target (e.g., in situations where there are multiple targets and/or multiple stimulations to treat a particular clinical application).

Unless otherwise specified herein, motor threshold (MT) is determined using standard methods known to those of skill in the art. For example, in typical prior art methods for stimulation of brain regions at or near the cortical surface, the TMS electromagnet is placed over the motor cortex (on the side of the patient's head) and particularly the region mapping to the subject's hand, and power is applied to determine the minimum amount of power necessary to evoke an involuntary movement of the subject's hand. The minimum power to cause the involuntary movement is the motor threshold. Treatments are then typically indexed off of the motor threshold amount; in most prior art applications, stimulation is generally between about 110% and 120% MT to stimulate the cortical surface. In the variations described herein in which multiple (e.g., an array) of TMS electromagnets are used to stimulate deep-brain regions, the MT may be determined using one of the magnets from the array; typically the most efficient TMS electromagnet is used, and MT is determined as indicated above, by placing the TMS electromagnet over the region of motor cortex controlling hand movement to determine the threshold. For example, when an array of TMS electromagnets are used, the primary (e.g., central TMS electromagnet), which may be a swept-wing coil, may be used. Alternatively, in some variations the MT for each TMS electromagnet may be determined individually.

As described herein, we consider the combined stimulation at a deep target to be less that 100% of MT based primarily on the fall off from the TMS Electromagnet coils; in some variations, the 'actual' stimulation seen by the deep brain target may be at or above MT if actually measured. The membrane of a given neuron may be partially depolarized (e.g., depolarized to a place closed to its threshold) making it easier to fire, whether due to further depolarization from its normal neural inputs or from direct impact of the imposed magnetic field. This may be more likely to occur in highly conductive nerve tracts like the cingulate and areas adjacent to cerebrospinal fluid conduits. Interconnected nerve tracts such as the cingulate and other tract structures may thereby capture more power/signal from the stimulation, and result in a greater probability of excitation.

The methods described herein may include a step of identifying and focusing on or directing the TMS electromagnet(s) to the deep brain target or targets. For example, the methods may include the step of orienting a plurality of TMS electromagnets so that their theoretical fields converge on a deep brain target or on one or more tracts that communicate directly with the deep brain target. The tract may be a nerve bundle.

BRIEF DESCRIPTION OF THE DRAWINGS

FIGS. 2A-2C show transverse, coronal, and saggital views, respectively, of brain activity in a control (sham) trial in a subject.

FIGS. 2D-2F show transverse, coronal, and saggital views, respectively, of brain activity in the same subject when stimulating at less than 100% MT for all of the TMS electromagnets in the array.

FIGS. 3A and 3B show tables indicating the experimental applied stimulator power used for typical subjects.

DETAILED DESCRIPTION OF THE INVENTION

Figure 1A:
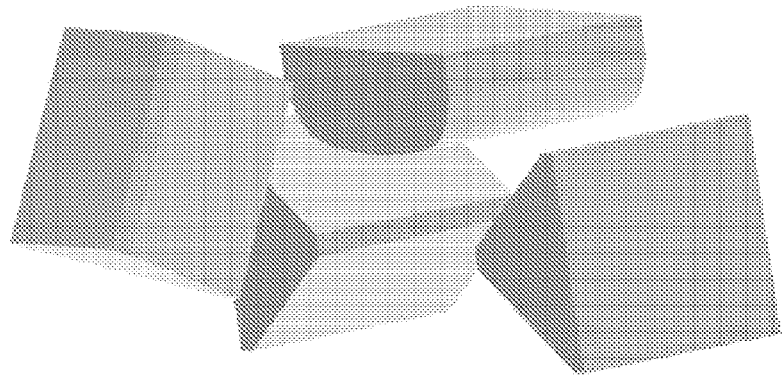
FIG. 1A is a schematic of one variation of a system for deep brain stimulation as described herein. In this variation the system includes four TMS electromagnets of various configurations on a gantry that allows them to be positioned around the subject's head oriented at a deep-brain target.

One variation of an experimental set-up is illustrated in FIG. 1A. FIG. 1A illustrates a TMS system including four TMS electromagnets. In FIG. 1A, the CAD model illustrates an arrangement of magnets which may be referred to as a "diamond array." The subject's head and any electromagnet coil fixation device are not shown in this figure. These four TMS electromagnets may be connected to a scaffold, gantry, or other fixation device. In FIG. 1A, the center, top TMS electromagnet is a swept-wing coil and the two lateral coils are V-Coils in the same vertical plane. A third V-Coil is located anteriorly, swinging down and configured to touch the subject's forehead.

Figure 1B:
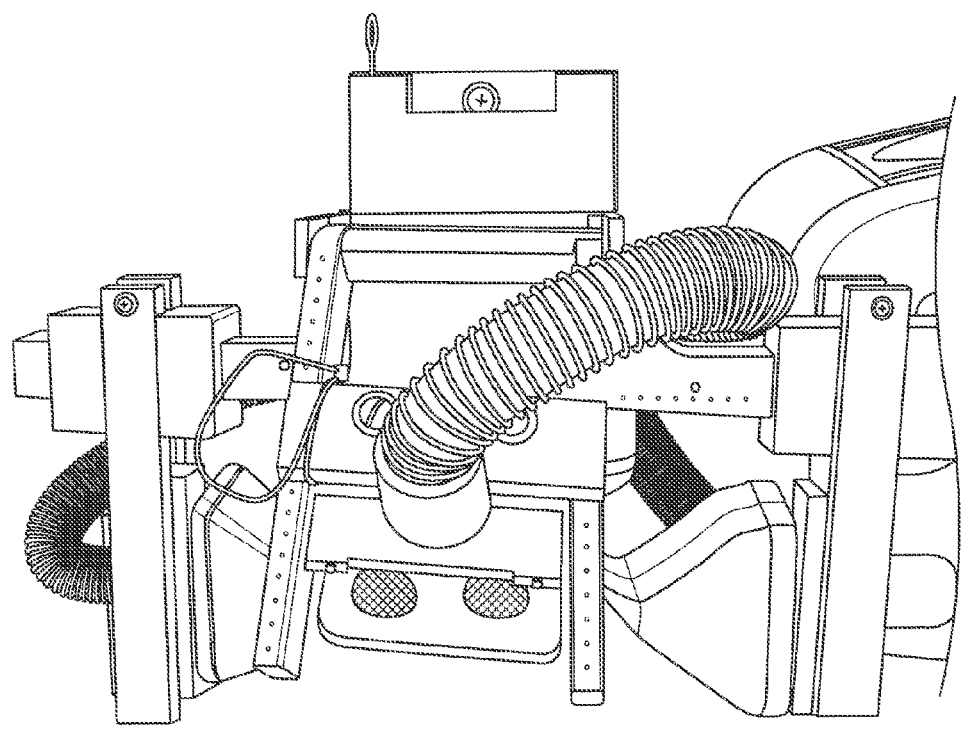
FIGS. 1B-1C show another embodiment of a system as described herein from different orientations.
Figure 1C:
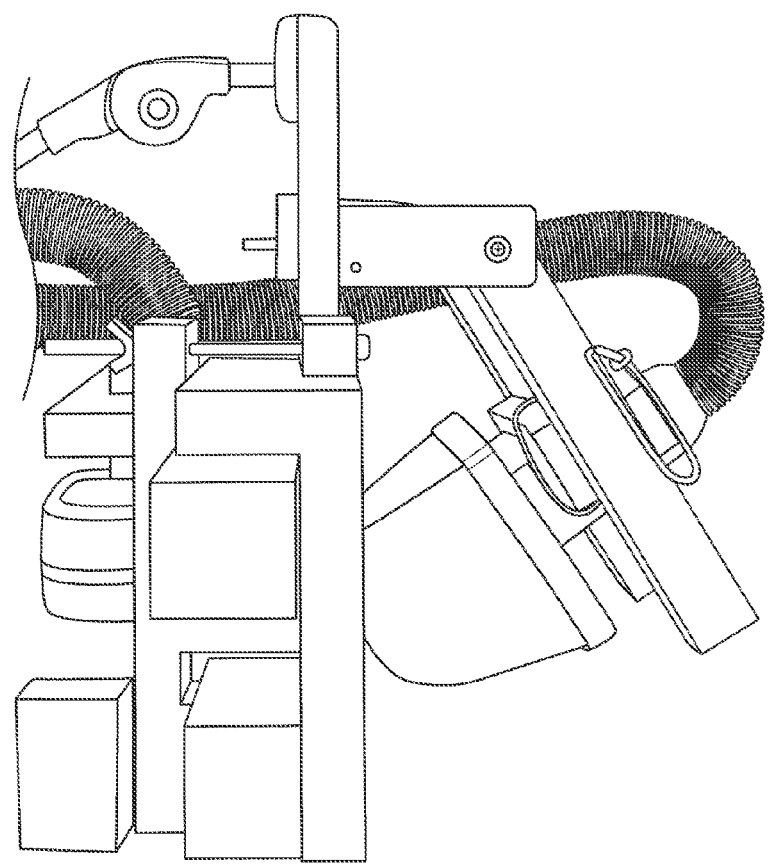
Figure 1D:
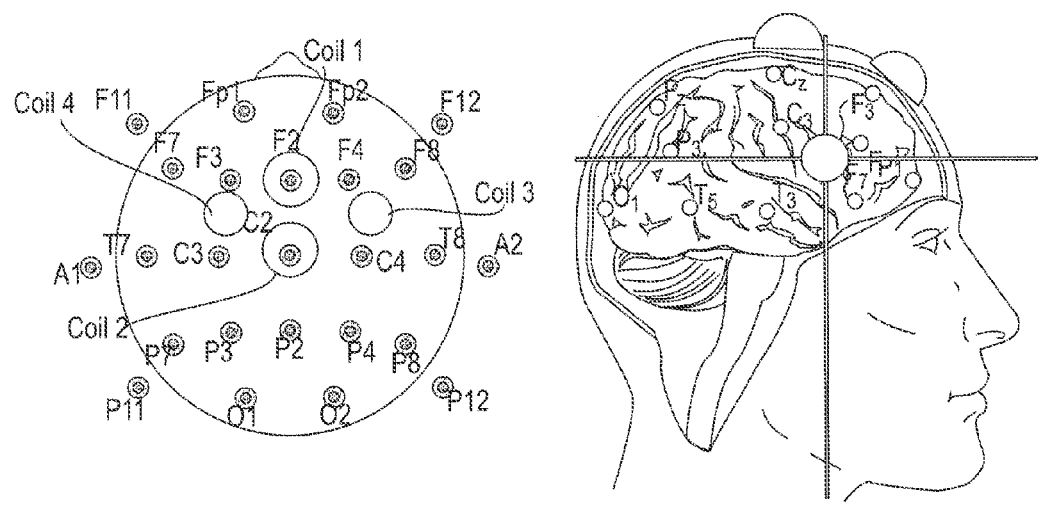
FIG. 1D shows a four-part illustration of an arrangement of the locations of TMS electromagnets targeting the cingulate tracts that may be used based on EEG electrode placement spatial descriptors.
Figure 1D:
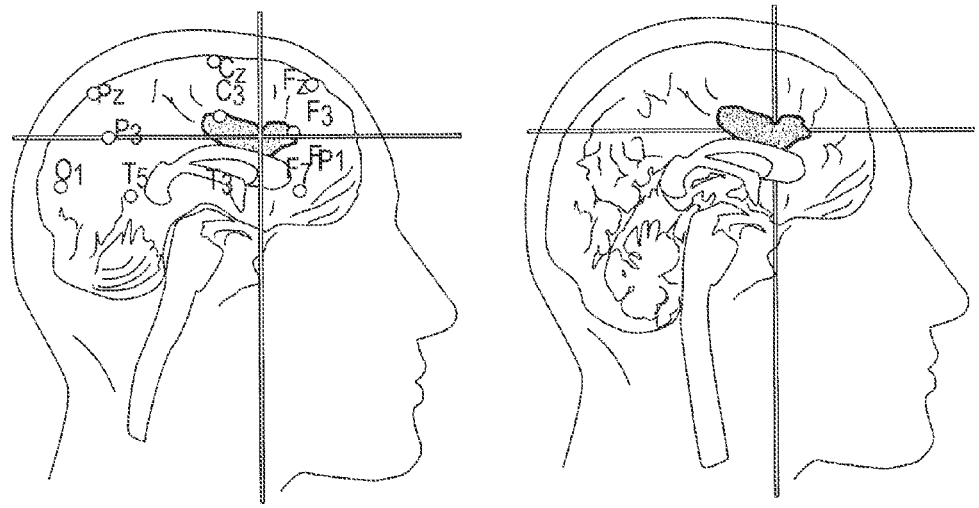

FIGS. 1B to 1C illustrate a system such as the one shown in FIG. 1A. For example, FIG. 1B shows a front view of such a system and FIG. 1C shows a side view. FIG. 1D shows a diamond-array configuration of a TMS system relative to standard EEG placement landmarks. The centers of the electromagnets are located at the landmarks. For example, in the upper and lower left quadrant of FIG. 1D, four TMS electromagnets are represented as large (but possibly not as large as the electromagnets themselves) hemispheres positioned about the subject's head. The upper and lower right quadrants of FIG. 1D show exemplary sections (e.g., sagittally-sectional scans) illustrating the deep-brain penetration of one variation of a diamond-array of TMS electromagnets in the cingulated gyms region of a brain.

In one example, a protocol using the configuration shown in FIGS. 1A-1D may be used to stimulate a deep brain region at sub-MT levels sufficient to modify function of the deep brain structure. An array of TMS electromagnets may be stimulated at a stimulation rate of 1 Hz, applied simultaneously to all the magnets. For example, a Magstim Rapid stimulator and a custom LabVIEW software program may be used to trigger the stimulators via a computer control port on each of the four stimulators. The tables shown in FIGS. 3A and 3B illustrate power profiles that may be applied to achieve sub-MT modulation of deep brain targets. The effect of such stimulation profiles in this example can be monitored by PET scans, as illustrated in FIG. 2.

Figure 3C:
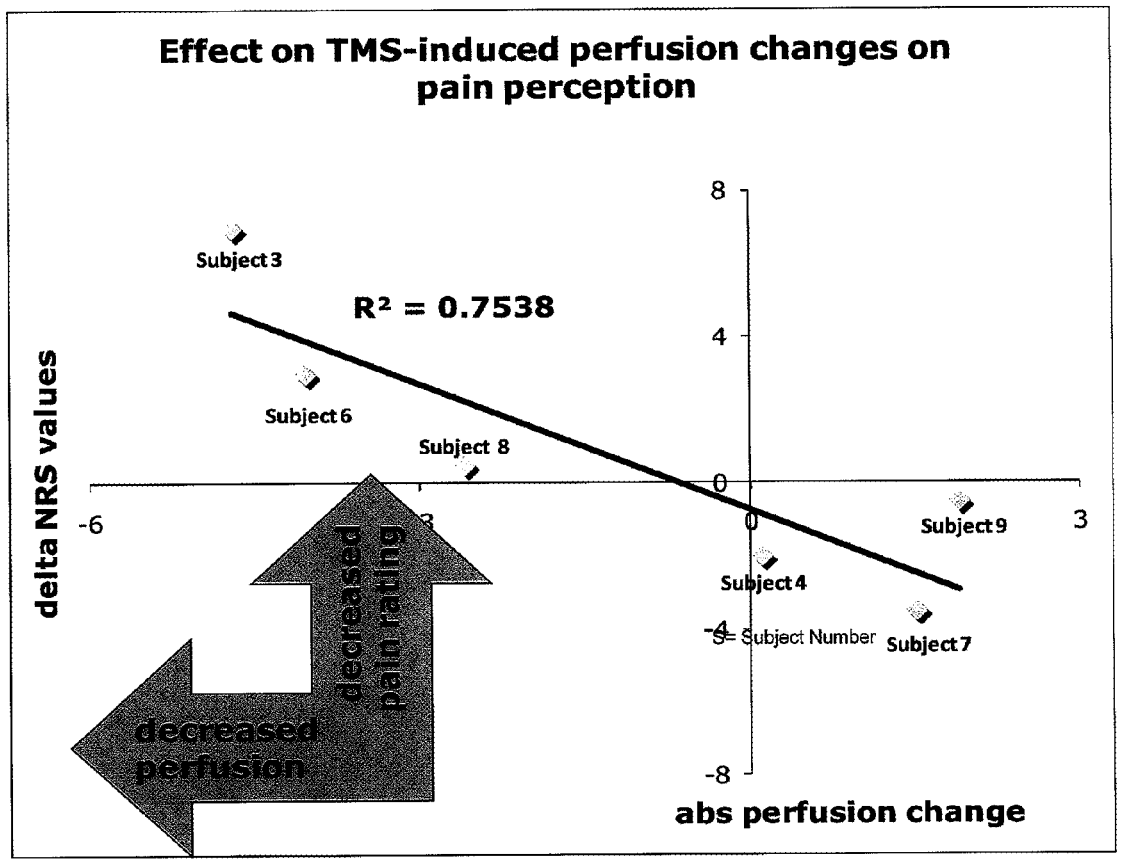
FIG. 3C illustrates the strong correlation between the level of blood perfusion and the perceived pain level in subject's undergoing TMS stimulation.

Note that the power applied (as illustrated in FIGS. 3A and 3B) is power applied to the coil, and not power at the target and that the % of power shown is the % that the stimulator puts on the given channel, not the % of Motor Threshold. The applied-power data shown in FIGS. 3A and 3B and FIG. 2 has a strong correlation between the level of blood perfusion, as demonstrated on PET scans with a pain level as perceived by a subject, obtained from an array of TMS electromagnets using these applied powers. In general, it is known that the level of blood perfusion correlates to the pain level perceived by the subject, as illustrated in FIG. 3C. (extracted from Yeomans DC and Tzabasis A). The activation of the these magnets around the patient's head causes activity in the target region to summate by one or more means including magnetic field overlap/superposition (physical summation), temporal summation, and spatial summation). The effect of sub-MT stimulation (e.g., subthreshold stimulation) may be demonstrated by the impact that the stimulation has on a deep brain structure. The effect of the stimulation on both the deep brain region and the intermediate (more cortical) regions may be seen by direct visualization. For example, FIG. 2 illustrates one example of this.

One variation of an experimental protocol used to stimulate at sub-MT conditions applies a 1 Hz stimulation (for 30 minutes) to one or a plurality of (e.g., all) TMS coils in an array of TMS electromagnets, such as a diamond array, as illustrated above in FIG. 1D. Power applied to any magnet in the four-magnet array in this example does not exceed 100% of Motor Threshold. The effect of such a stimulation protocol may be monitored, as mentioned above, by scans (e.g., PET scans) and/or by patient reporting. For example, in some variations the effect of TMS stimulation at sub-MT levels may be monitored by measuring an index of pain. In an exemplary pain monitoring method, the skin is sensitized with capsaicin, and the heat-induced pain threshold and tolerance are determined using a Peltier thermode over a sensitized area. Scans are taken when pain is induced at 60% of tolerance during the PET scans, following a real or sham treatment, using a Peltier thermode at constant temperature over a sensitized area. Verbal reports on pain level are received every 1 minute during scans. The threshold and tolerance may be re-assessed after each scan.

PET imaging may also be performed. A typical protocol for PET imaging may include Regional Cerebral Blood Flow (rCBF) estimation using 150-H2O PET/CT. For example, a GE Discovery VCT PET/CT scanner may be used. 10 minutes of dynamic acquisitions (no arterial blood samples) can be taken, and dynamic frames at [12×10 s, 4×30 s, 2×60 s, 1×90 s, 1×150 s] may be acquired. The settings may include: 3D acquisition, 30 cm diameter transverse FOV, 15 axial FOV. The images may be reconstructed using parameter settings of: ordered Subsets Expectation Maximization (OS-EM) with 4 iterations/24 subsets; corrections include measured (CT) attenuation correction (AC); 4 mm FWHM Gaussian post-filter; four scans per session: baseline, pain with sham intervention, re-baseline or pain with no intervention, and pain with real intervention. Volumes of interest may be analyzed.

FIG. 2A-2C show views of an un-stimulated (or sham-stimulated) subject's brain activity from transverse, coronal, and saggital views. In this example, the image is pseudo-colored (e.g., shaded) to show brain activity, darker being low levels of blood flow, and lighter being high levels of blood flow.

As mentioned, the tables in FIGS. 3A and 3B show powers applied in similar experiments on two other patients. Each of four TMS electromagnets was stimulated at a power level indicated in the table (as a percent of stimulator output). The percentage of stimulator power applied corresponding to motor threshold for each patient was determined as part of the procedure. In FIG. 3A, the % power corresponding to MT was 80%, while in FIG. 3B, the percent power corresponding to motor threshold was approximately 85% of the power of the stimulator. In subjects 1 & 2, stimulation above MT was never used. Unexpectedly, in trials performed to examine the diamond configuration described above, most subjects only went over threshold stimulation at the very end of the session; most of the session was sub-MT threshold. The two patients illustrated in FIGS. 3A and 3B did not exceed the MT based on expected power at the deep brain region. This sub-MT stimulation effectively modulated the activity of the deep brain target(s), as determined by the imaging made on these two patients (corresponding to the applied powers in FIGS. 3A and 3B), and based on two outcome measures: (1) blood perfusion levels of different areas of the brain (corresponding to metabolic rate of those areas of the brain) when compared to placebo, and (2) patient ratings of pain levels. The metabolic activity in the target deep brain region (the cingulate) is directly linearly proportional to the amount of pain that the patient is experiencing. The stimulation applied at the power levels shown in FIGS. 3A and 3B resulted in inhibiting activity in cingulate during the real treatment (which was visible by PET, similar to the illustration shown above for FIG. 2).

Figure 4:
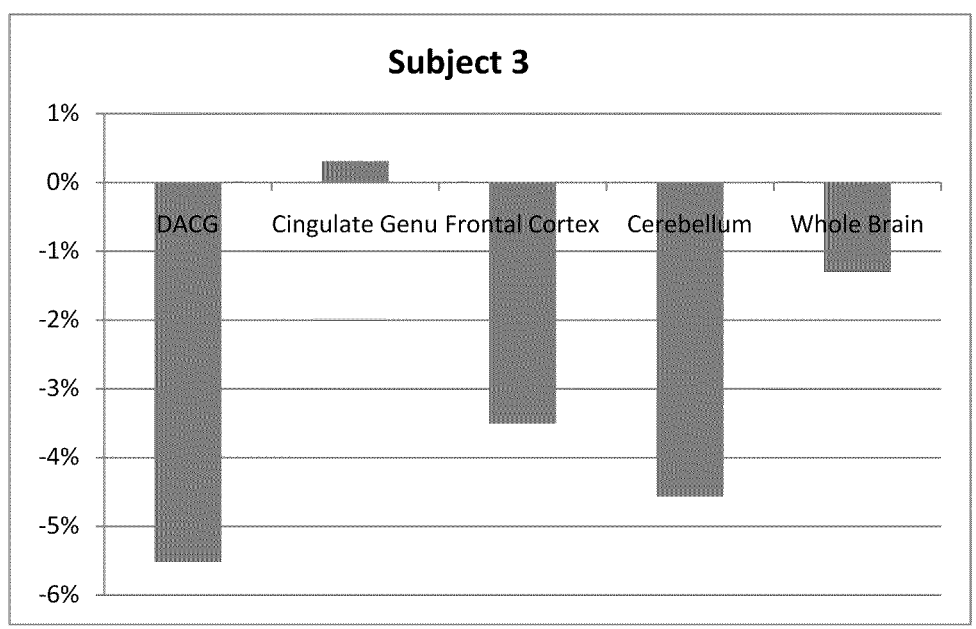
FIG. 4 shows a summary graph indicating the modulation of different brain regions using the sub-threshold (sub-MT) stimulation for one subject using the array of the system described herein. This figure shows brain perfusion changes in sham vs. real conditions from 20-80 seconds following intravenous infusion of 15-O/water.

FIG. 4 summarizes the effect of sub-MT stimulation in subject such as those illustrated above to different brain regions. For example, in experimental data, the target deep-brain regions include the DACG (Dorsal Anterior Cingulate Gyms) and the Cingulate Genu. The comparison region is the Frontal Cortex which is an area that is in general less impacted by the magnetic field, demonstrating that there is a preferential effect on the cingulate and the comparison to reference regions represented by the cerebellum and whole brain that would not be expected to be impacted significantly with the kind of focused targeting described herein.

The data in FIG. 4 were generated by determining the activity from differences in activity of Oxygen-15 labeled water as measured in the PET scan.

The examples above illustrate the effect of sub-MT stimulation of deep brain target regions using an array of TMS electromagnets. A similar effect may also be observed using only a single TMS electromagnet. For example, a single TMS electromagnet may be used to stimulate brain target by applying power at sub-MT threshold levels. The inherent inadvertent stimulation of non-target sites is a typical limitation of single-coil approaches.

This result confounds conventional wisdom on neurotherapy. Although it may have been known that one did not need 100% or more of Motor Threshold at the cortical surface to obtain a therapeutic effect (e.g., known with a single coil to modulate), it has not been proposed that deep brain stimulation at similar sub-MT levels would result in an appreciable effect. Moreover, based on the stimulation of cortical structures, and the known fall-off of TMS electromagnets at depth, it is particularly surprising that any modulatory effect would be seen at deep brain regions giving sub-MT power levels.

During the experiments described above, it was noted that neuromodulation at deep target at power less than subcortical MT levels was occurring, despite the expectations based on previously described systems.

The observation that modulation of deep brain targets can occur at sub-MT power levels (e.g., levels much lower than previously anticipated) has numerous implications to the design and operation of effective and efficient TMS systems.

Generally this means that when using one or more TMS electromagnet to target a deep brain (e.g., non-cortical) target, the one or more magnet should be oriented towards the deep brain target directly, and the magnet (or magnets) stimluated at a power level that may be sub-MT at the target. In some variations the power is sub-MT for more superficial brain regions (e.g., between the magnet(s) and the target) as well. The step of aiming or orienting may involve positioning the face of the magnet(s) around the subject's head at an angle with respect to the subject's head so that the emitted field is oriented toward the deep-brain target regions rather than, for example, in an orientation perpendicular to the patient's skull.

In one example, the operation of a system configured to stimulate deep-brain targets includes the step of focusing or aiming the one or more TMS electromagnets as a deep brain target (or a target that applies modulatory input directly to the deep brain target). In particular, the TMS electromagnet(s) may be oriented towards the deep brain target by changing the angle of the electromagnet relative to the head. Aiming the coil at deeper tissues (rather than at superficial tissues) may deliver more power to the target.

As mentioned, the angle of the face of the magnet with respect to the head may be maximized so that the face or apex of the magnet is oriented to maximally impact the deeper tissue. In general, this means that the center axis or axes of the magnet or magnets (and thus the center axis of the emitted magnetic field) are directed toward a deep brain target. In some variations, the angle of the magnet is movable relative to the subject's head to orient towards a deep brain target.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. Such modifications and changes do not depart from the true spirit and scope of the present invention.

What is claimed is:

1. A method of modulating a deep brain target using low power stimulation, the method comprising:
    aiming a plurality of TMS electromagnets at a deep brain target; and
    applying power to each of the TMS electromagnets at a level that is below the motor threshold (MT) at the target, thereby modulating the activity of the deep brain target.

2. The method of claim 1, further comprising identifying the deep brain target.

3. The method of claim 1, wherein the step of aiming comprising orienting the apex or face of each TMS electromagnet so that the central axis of the applied magnetic field intersects the target.

4. The method of claim 1, wherein the deep brain target is the cingulate.

5. The method of claim 1, wherein the deep brain target is the insula.

6. The method of claim 1, wherein the power applied to one or more TMS electromagnets is below the motor threshold for neuronal regions between the target and the plurality of TMS electromagnets.

7. A method of treating a disorder by deep brain transcranial magnet stimulation, the method comprising:
    identifying a target deep brain region associated with the disorder;
    aiming a TMS electromagnet at the target deep brain region; and
    applying power to the TMS electromagnet at a level that is below the motor threshold (MT) at the target deep brain region to modulate the activity of the target deep brain region.

8. The method of claim 7, further comprising aiming a second TMS electromagnet at a neuronal target.

9. The method of claim 8, wherein the neuronal target modulates the activity of the target deep brain region.

10. The method of claim 8, further comprising up-regulating both the target deep brain region and the neuronal target.

11. The method of claim 8, further comprising down-regulating the target deep brain region and the neuronal target.

12. The method of claim 8, further comprising up-regulating the target deep brain region and down-regulating the neuronal target.

13. The method of claim 7, wherein the target deep brain region is the cingulate.

14. The method of claim 7, wherein the target deep brain region is the insula.

15. The method of claim 7, wherein the disorder is selected from the group consisting of: pain, depression, addiction, Alzheimer's disease, attention deficit disorder, autism, anorgasmia, cerebral palsy, bipolar depression, unipolar depression, epilepsy, generalized anxiety disorder, acute head trauma, hedonism, obesity, OCD, acute pain, chronic pain, Parkinson's disease, persistent vegetative state, phobia, post-traumatic stress disorder, rehabilitation/regenesis for post-stroke, post- head trauma, social anxiety disorder, Tourette's Syndrome, hemorrhagic stroke, and ischemic stroke.

16. A method of treating a disorder by deep brain transcranial magnet stimulation, the method comprising:
    identifying a target deep brain region;
    aiming a plurality of TMS electromagnets at the target deep brain region; and
    applying power to the plurality of TMS electromagnets at a level that is below the motor threshold (MT) at the target deep brain region to modulate the activity of the target deep brain region.

* * * * *